United States Patent [19]
Hong et al.

[11] Patent Number: 5,821,605
[45] Date of Patent: Oct. 13, 1998

[54] LOC SEMICONDUCTOR PACKAGE

[75] Inventors: Joon Ki Hong; Dong Seok Chun, both of Chungcheongbuk-do, Rep. of Korea

[73] Assignee: LG Semicon Co, Ltd., Chungcheongbuk-do, Rep. of Korea

[21] Appl. No.: 510,233

[22] Filed: Aug. 2, 1995

[30]       Foreign Application Priority Data

May 12, 1995 [KR] Rep. of Korea ........................ 95-11774

[51] Int. Cl.⁶ .................................................. H01L 23/48
[52] U.S. Cl. ............................ 257/666; 257/668; 257/691
[58] Field of Search .................................... 257/666, 668, 257/669, 676, 691, 787

[56]             References Cited
           U.S. PATENT DOCUMENTS

5,227,232  7/1993  Lim .......................................... 257/670
5,286,999  2/1994  Chiu ......................................... 257/666

*Primary Examiner*—Peter Toby Brown

[57]              ABSTRACT

A semiconductor package is disclosed including a semiconductor chip having a plurality of bonding pads on its top surface; a plurality of inner leads located above the semiconductor chip and electrically connected to the bonding pads by wire; a plurality of outer leads extending from the respective inner leads; and at least one bus bar for power supply and ground formed to be lower than the inner leads above the semiconductor chip. A method of packaging a semiconductor device is disclosed including the steps of: providing a semiconductor chip having a plurality of bonding pads on its top surface; arranging a plurality of inner leads and a plurality of outer leads extending therefrom above the semiconductor chip; and arranging bus bars for power supply and ground to be lower than the inner leads above the semiconductor chip.

12 Claims, 10 Drawing Sheets

LOC SEMICONDUCTOR PACKAGE

BACKGROUND OF THE INVENTION

The present invention relates to a semiconductor package and a method of packaging a semiconductor device. More particularly, the present invention relates to a semiconductor package and a method of packaging a semiconductor device suitable for a lead-on-chip (LOC) structure.

Figure 1:
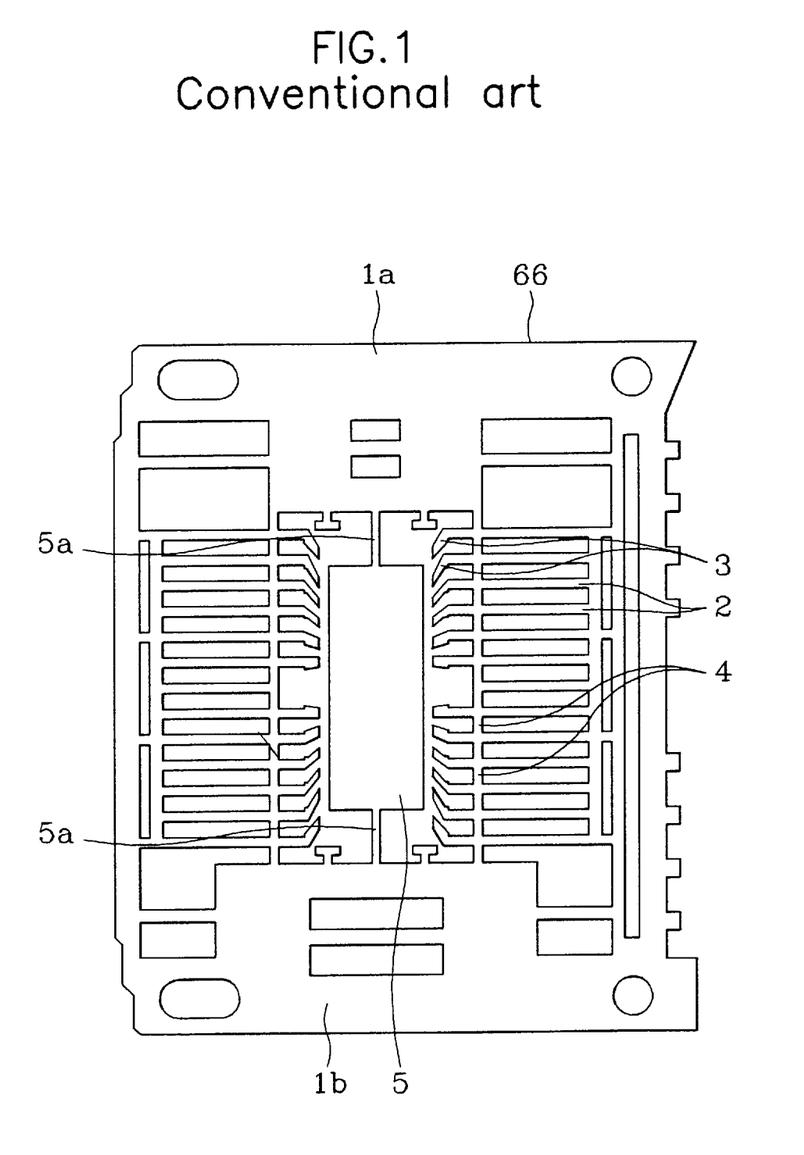
FIG. 1 is a configuration diagram of a lead frame generally used in a semiconductor package.

Firstly, the structure of a lead frame 66 used in a conventional semiconductor package will be discussed with reference to FIG. 1. In FIG. 1, side rails 1a and 1b are placed on the upper and lower sides of a lead frame 66. A plurality of outer leads 2 and inner leads 3 are located between side rails 1a and 1b. A dam bar 4 functions to support the outer leads 2 and inner leads 3 between upper and lower side rails 1a and 1b. A paddle 5 (on which a semiconductor chip is to be put) is placed at the center of the lead frame 66. A support bar 5a acts to support paddle 5 between side rails 1a and 1b.

Figure 2:
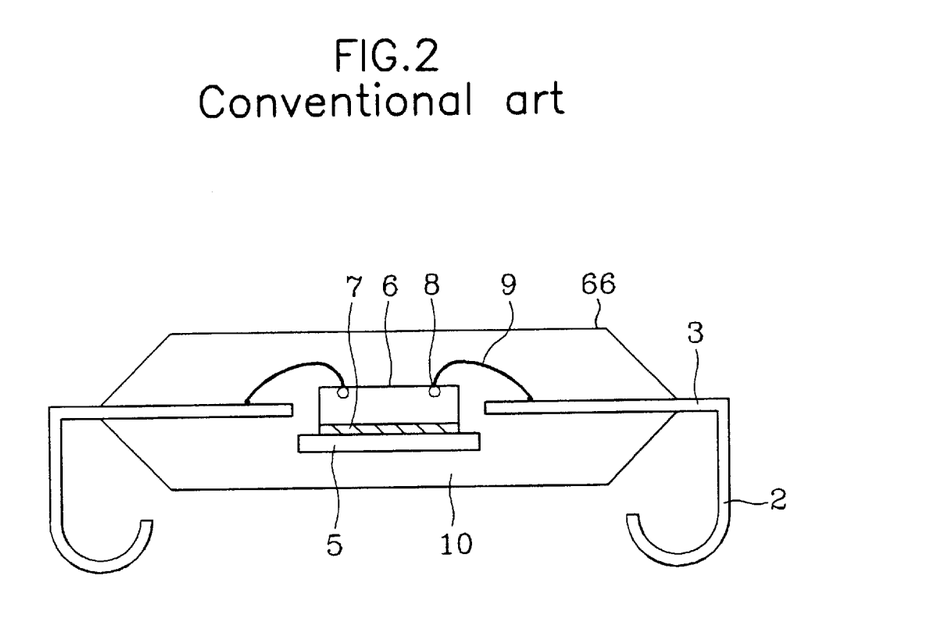
FIG. 2 is a sectional view of a conventional semiconductor package.

The structure of a semiconductor package made by using the lead frame 66 of FIG. 1 will be explained with reference to FIG. 2. Referring to FIG. 2, a semiconductor chip 6 is attached onto paddle 5 of the lead frame 66 using an epoxy adhesive 7. Bonding pads 8 formed on the top surface of semiconductor chip 6 and inner leads 3 of the lead frame 66 are conductively connected with metal wires 9. Subsequently, except for outer leads 2, all of the other elements are encapsulated with epoxy molding compound 10, to thereby make the semiconductor package. Finally, outer leads 2 are formed in a desired shape. In FIG. 2, the outer leads 2 are J-shaped.

In the structure of FIG. 2, the upper surface of the semiconductor chip 6 is positioned in a plane defined above the plane of the encapsulated portion of the inner leads 3. As a result, the metal wires 9 must be bent a greater degree in connecting the outer leads 2 to the bonding pads 8 than if the degree of separation between the planes were less resulting in switching of the metal wire 9 during the molding process. This condition results in deterioration of the electrical signal transmission characteristics of the metal wire 9 or, in some cases, a short-circuit. In addition, there has arisen a need to remove paddle 5 of the lead 66 frame as the capacity of a semiconductor package becomes larger.

An LOC semiconductor package has been proposed to overcome such problems. As discussed above with regard to FIG. 2, the top surface of semiconductor 6 is placed above the plane of the inner leads 3. Conversely, in the LOC semiconductor package, the inner leads are placed on the top surface of the semiconductor chip. Instead of the paddle 5 of the lead frame 66, an adhesive insulation tape is used to attach the bottom surface of the inner leads to the top surface of the semiconductor chip. An example of such an LOC semiconductor package will be discussed in detail with reference to FIGS. 3–6.

Figure 3:
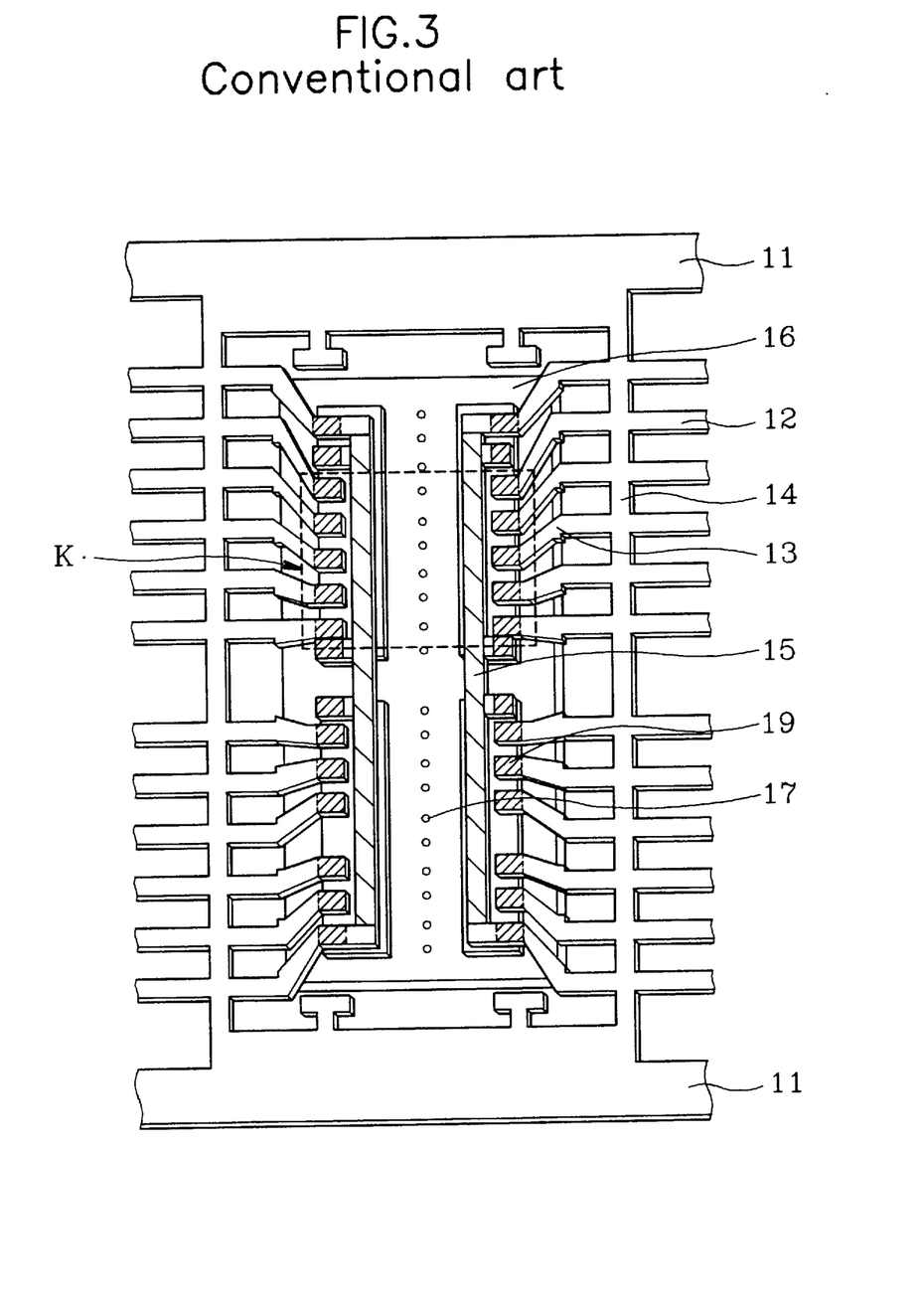
FIG. 3 is a configuration diagram of an LOC lead frame used in a conventional LOC semiconductor package.

FIG. 3 is a diagram of the structure of an LOC lead frame used in an LOC semiconductor package. Side rails 11 are placed above and under the lead frame 77. A plurality of outer leads 12 and inner leads 13 occur between side rails 11 located above and under the lead frame 77. Outer leads 12 and inner leads 13 are supported between upper and lower side rails 11. The respective distances between the outer and inner leads is maintained by dam bar 14.

Bus bars 15 extending from a portion of the plurality of inner leads 13 function as a common ground lead or a common power supply lead for supplying power to the semiconductor chip 16 and outer leads 12.

The top surface of double-sided adhesive insulation tape 17 adheres to the bottom surface of the front end of inner leads 13. The bottom surface of the adhesive insulation tape 17 is attached to the top surface of semiconductor chip 16. A metal coating 19 is placed on the top surface of the front end of inner leads 13 so that the inner leads are electrically connected to bonding pads 18 of semiconductor chip 16 by wires 20 (See FIG. 4).

Figure 4:
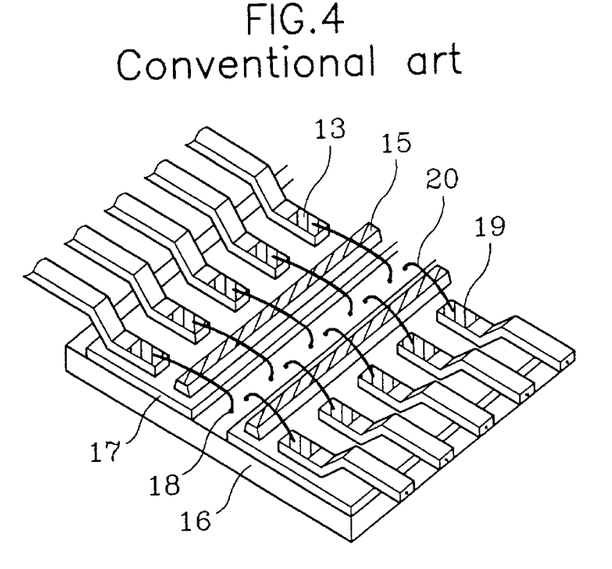
FIG. 4 is an enlarged view of area K of FIG. 3.

FIG. 4 is an enlarged view of the area K of FIG. 3. In FIG. 4, a plurality of inner leads 13 and bus bars 15 (used as the common ground lead or common power supply lead) are attached to the top surface of semiconductor chip 16 by the double-sided adhesive tape 17. The upper surfaces of the bus bars 15 extending from a portion of the inner leads 13 are placed between inner leads 13 and bonding pads 18 of semiconductor chip 16 at the same height as inner leads 13. Bonding pads 18 of semiconductor chip 16 and inner leads 13 are coupled electrically by wires 20.

Figure 5:
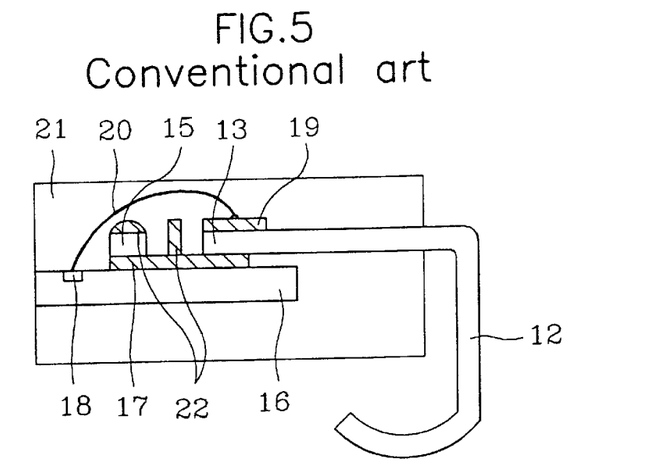
FIG. 5 is a sectional view of a conventional LOC semiconductor package.

FIG. 5 is a sectional view of the structure of a completed LOC semiconductor package. In FIG. 5, the bottom surface of the front end of a plurality of inner leads 13 and bus bars 15 are attached by the double-sided adhesive tape 17 to the top surface of semiconductor chip 16. Outer leads 12 are formed in a J-shape. Wires 20 electrically connect the front end of inner leads 13 (with metal coating 19) to bonding pads 18 of semiconductor chip 16. Inner leads 13 and bus bars 15 of the lead frame 77 are made of the same material (such as an alloy iron and nickel). The above-described structure can be varied with the arrangement of bonding pads 18 formed on the top surface of semiconductor chip 16.

In order to prevent an electric short in connecting each of the bonding pads 18 with a corresponding inner lead 13 using a wire 20, an insulating wall 22 is positioned on the upper surface of the adhesive tape 17 between the inner leads 13 and bonding pads 18. The insulating wall is higher than the upper surfaces of the inner lead 13 and bus bar 15. An insulator 22a is also formed on a portion of the top surface of bus bar 15 over which wires 20 pass.

Figure 6:
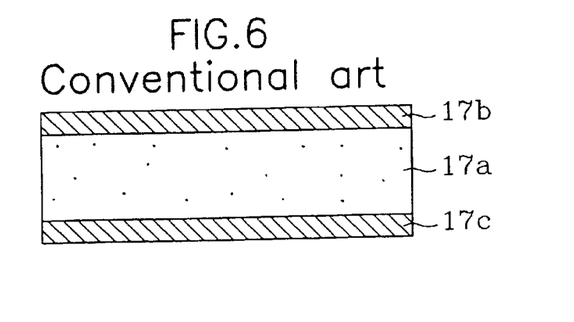
FIG. 6 is a configuration diagram of the double-sided adhesive tape of FIG. 5.

FIG. 6 is a sectional view of the double-sided adhesive tape 17 of FIG. 5. This tape is composed of a base film 17a of polyamide and adhesives 17b, 17c made of a thermoplastic material which is provided on the top and bottom surfaces of base film 17a. Here, the base film 17a is usually 50 µm thick. Adhesives 17b and 17c are about 25 µm thick. Therefore, the width of the double-sided adhesive tape 17 is about 100 µm. A die bonding process for attaching the top surface of semiconductor chip 16 to the lower adhesive 17c of the double-sided adhesive tape 17 is usually performed by thermal compression.

The above-discussed conventional technology has the following drawbacks.

Firstly, in the conventional LOC semiconductor package, since the bus bars 15 and inner leads 13 are of substantially the same height when attached to the upper adhesive of double-sided adhesive tape 17, the wires 20 must pass over the bus bars 15 in wire-bonding the inner leads 13 and bonding pads 18. Since the wires 20 may sag or be swept during the molding process, the wires 20 may come into contact with the bus bars 15, creating an electric short between the inner leads 13 and bus bars 15.

Secondly, in the case of a particularly thin semiconductor package, it is hard to control the height of the wires 20 for connecting the inner leads 13 and bonding pads 18 thereby increasing the possibility of an electric short between the wires 20 and bus bars 15. In order to prevent a short, an insulator 22a (FIG. 5) must be coated on the top surface of the bus bars 15, and/or an insulation wall 22 (with sufficient) positioned on the insulating tape to separate the inner leads 13 and bus bars 15, as shown in FIG. 5. The process of forming the insulating barriers for preventing a short circuit further complicates the manufacturing process and, accordingly, increases the production cost.

Thirdly, when the insulator for preventing a short between the inner leads 13 and bus bars 15 is coated, the insulator may run down to the inner leads 13. In this case, the inner leads 13 become contaminated, reducing the reliability of the inner leads 13.

Fourthly, in coating the insulator, void bubbles and water infiltration may occur, causing cracks in the semiconductor package. Accordingly, this decreases the reliability of the semiconductor package.

Thus, there are many disadvantages associated with conventional semiconductor devices and manufacturing processes.

SUMMARY OF THE INVENTION

Therefore, it is an object of the present invention to provide a semiconductor package and a method of packaging a semiconductor device for preventing a short circuit of a connecting wire in the area between bus bars and inner leads for increasing the device's reliability.

To accomplish the primary object of the present invention, the following is provided:

a semiconductor package including a semiconductor chip having a plurality of bonding pads on its top surface, a plurality of inner leads located above the semiconductor chip and electrically connected to the bonding pads by wires, a plurality of outer leads extending from respective inner leads and at least one bus bar (for power supply and ground) formed in a plane lower than a plane in which the inner leads exist above the semiconductor chip; and a method of packaging a semiconductor device having the steps of providing a semiconductor chip having a plurality of bonding pads on its top surface, arranging a plurality of inner leads and a plurality of outer leads extending therefrom above the semiconductor chip and arranging bus bars for power supply and ground in a spaced place which is lower than a plane in which the inner leads exist above the semiconductor chip.

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE ATTACHED DRAWINGS

The present invention will become more fully understood from the detailed description given hereinbelow and the accompanying drawings which are given by way of illustration only, and, thus, are not limitative of the present invention, and wherein.

DETAILED DESCRIPTION OF THE INVENTION

Hereinafter, preferred embodiments of the present invention will be described in detail with reference to the attached drawings.

First Embodiment

Figure 7:
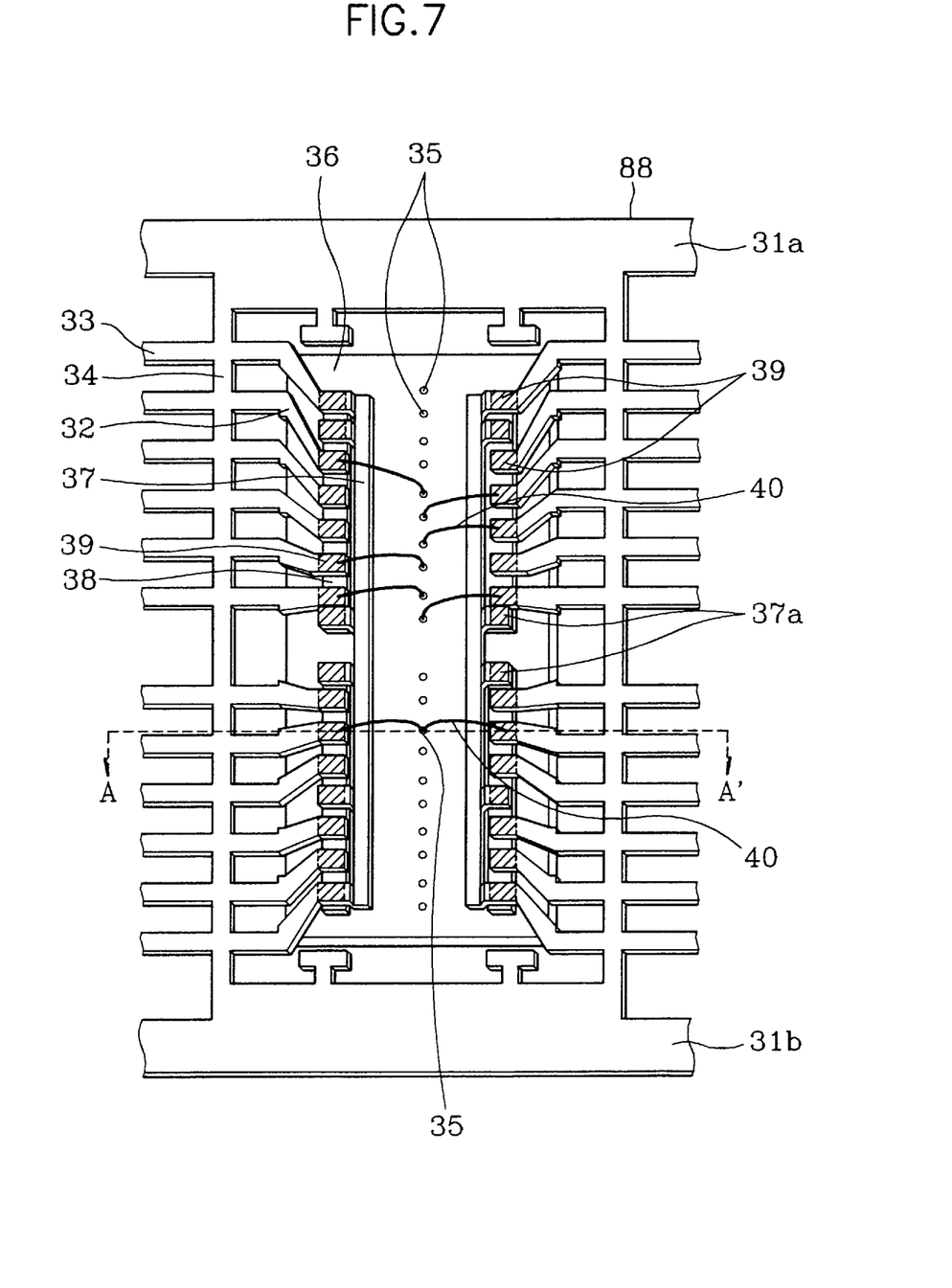
FIG. 7 is a configuration diagram of a first embodiment of an LOC lead frame on which a semiconductor chip is attached.

Referring to FIG. 7, the first embodiment of the lead frame 88 of the present invention includes upper and lower side rails 31a, 31b formed above and below the lead frame 88, inner and outer leads 32, 33 formed between upper and lower side rails 31a, 31b, a dam bar 34 for maintaining a desired distance between inner and outer leads 32, 33 and upper and lower side rails 31a, 31b, a semiconductor chip 36 located under inner leads 32 and having a plurality of bonding pads 35 on its top surface, bus bars 37 extending from selected inner leads 32 and having a plurality of bonding pads 35 on its top surface, bus bars 37 extending from part of inner leads 32 to between the other inner leads 32 and bonding pads 35 of semiconductor chip 36 and formed to be lower than inner leads 32 and having protrusions 37a extending toward inner leads 32, and an insulation double-sided adhesive tape 38 for attaching the bottom surface of the front end of inner leads 32 and protrusions 37a of bus bars 37 to the top surface of semiconductor chip 36.

A conductor 39 (such as silver) is coated on the top surface of the front end of inner leads 32 to facilitate wire bonding of the inner leads 32 to bonding pads 35 located on the top surface of semiconductor chip 36. Protrusions 37a of bus bars 37 have the same height as inner leads 32 in order to be attached to insulation double-sided adhesive tape 38 along with the front end of inner leads 32.

As explained previously with reference to conventional devices, the wire bonding is to electrically connect semiconductor chip 36 to inner leads 32, semiconductor chip 36 to bus bars 37 or bus bars 37 to outer leads 33. Outer leads 33 are formed to extend from respective inner leads 32.

The bus bars 37 may be manufactured with the lead frame 88, or separately made to be connected to part of inner leads 32 of the lead frame 88 after being attached to semiconductor chip 36.

Side rails 31a and 31b and dam bars 34 are removed before or after the molding of other package elements excluding outer leads 32.

In the first embodiment of the LOC lead frame for the LOC semiconductor package of the present invention, insulation double-sided adhesive tape 38, which is used in conventional devices to prevent an electric short between inner leads 32 and bus bars 37 when wire 40 comes into contact with bus bars 37 in wire bonding for electric connection between bonding pads 36 of semiconductor chip 36 and inner leads 32 is placed only under the front end of inner leads 32.

Therefore, the insulation double-sided adhesive tape 38 is not present in the area under the bus bars 37 extending between bonding pads 35 of semiconductor chip 36 and inner leads 32. Instead, bus bars 37 are subject to down-set processing. Bus bars 37 are formed to be lower than inner leads 32 by an amount approximately equal to the thickness of the insulation double-sided adhesive tape 38. In the configuration of FIG. 7, one, two or more bus bars 37 may be provided.

Figure 8:
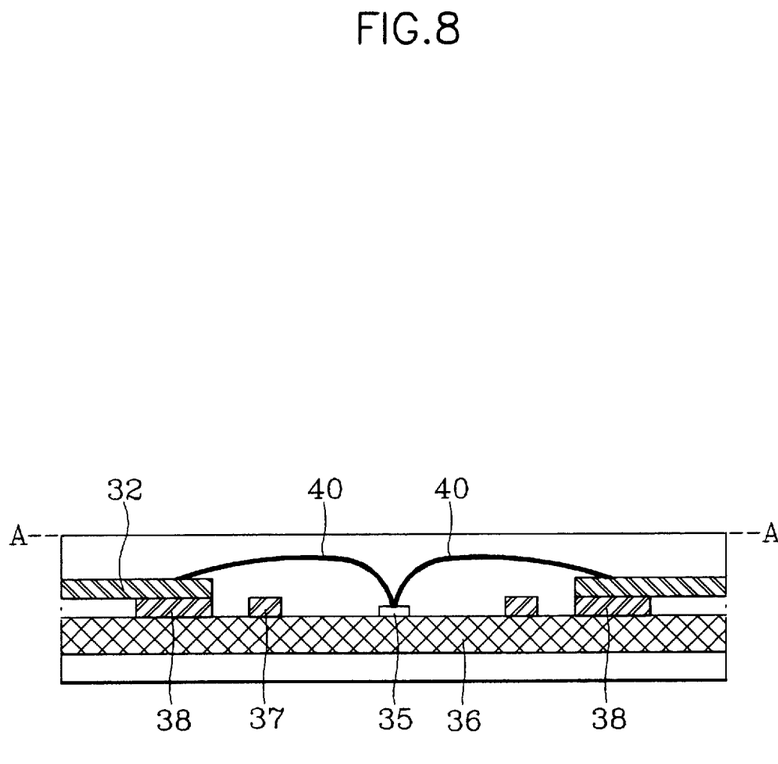
FIG. 8 is a sectional view of FIG. 7 along line A-A'.

Referring to FIG. 8, insulation double-sided adhesive tape 38 is placed only under the front end of inner leads 32 but not under the extending portion of bus bars 37. Instead, the extending portion is subject to down-set processing and becomes lower than inner leads 32 by an amount equal to the thickness of the double-sided adhesive insulation tape 38.

For this reason, in wire bonding for electrical connection between inner leads 32 and bonding pads 35, an electric short between inner leads 32 and bus bars 37 can be prevented, without forming an insulation wall or coating an insulator on the top surface of the bus bars 37.

For the final process, other package elements excluding outer leads 33 are molded in an epoxy molding compound to form a compound body and the exposed outer leads 33 are formed in a desired shape.

As described above, the first embodiment of the present invention has the following effects.

Firstly, since the extending portion of bus bars 37 placed between inner leads 32 and bonding pads 35 of semiconductor chip 36 is subject to the down-set processing, wire 40 for electrically connecting semiconductor chip 36 and inner leads 32 can be bonded in a low loop on semiconductor chip 36. This prevents an electrical short and increases the reliability of the thin semiconductor package.

Secondly, insulation double-sided adhesive tape 38 is not under bus bars 37 but under the front end of inner leads 32, reducing the production cost, as compared with the conventional art.

Thirdly, there is no need to coat an insulator such as polymer on the top surface of the bus bars unlike the conventional art. Eliminating the need for the insulator prevents voids and bubbles which may be created in manufacturing the semiconductor package and enhances the reliability of the semiconductor package.

Fourthly, since an insulator or insulation wall is not formed on the surface of the bus bars 37 or between the bus bars 37 and inner leads 32, the area in which the epoxy molding compound makes contact with the inner leads 32 and bus bars 37 in molding is increased, thereby enhancing the reliability of the thin semiconductor package.

Second Embodiment

Hereinafter, the second embodiment of the present invention of the LOC lead frame on which a semiconductor chip is attached will be described with reference to the attached drawings.

Figure 9:
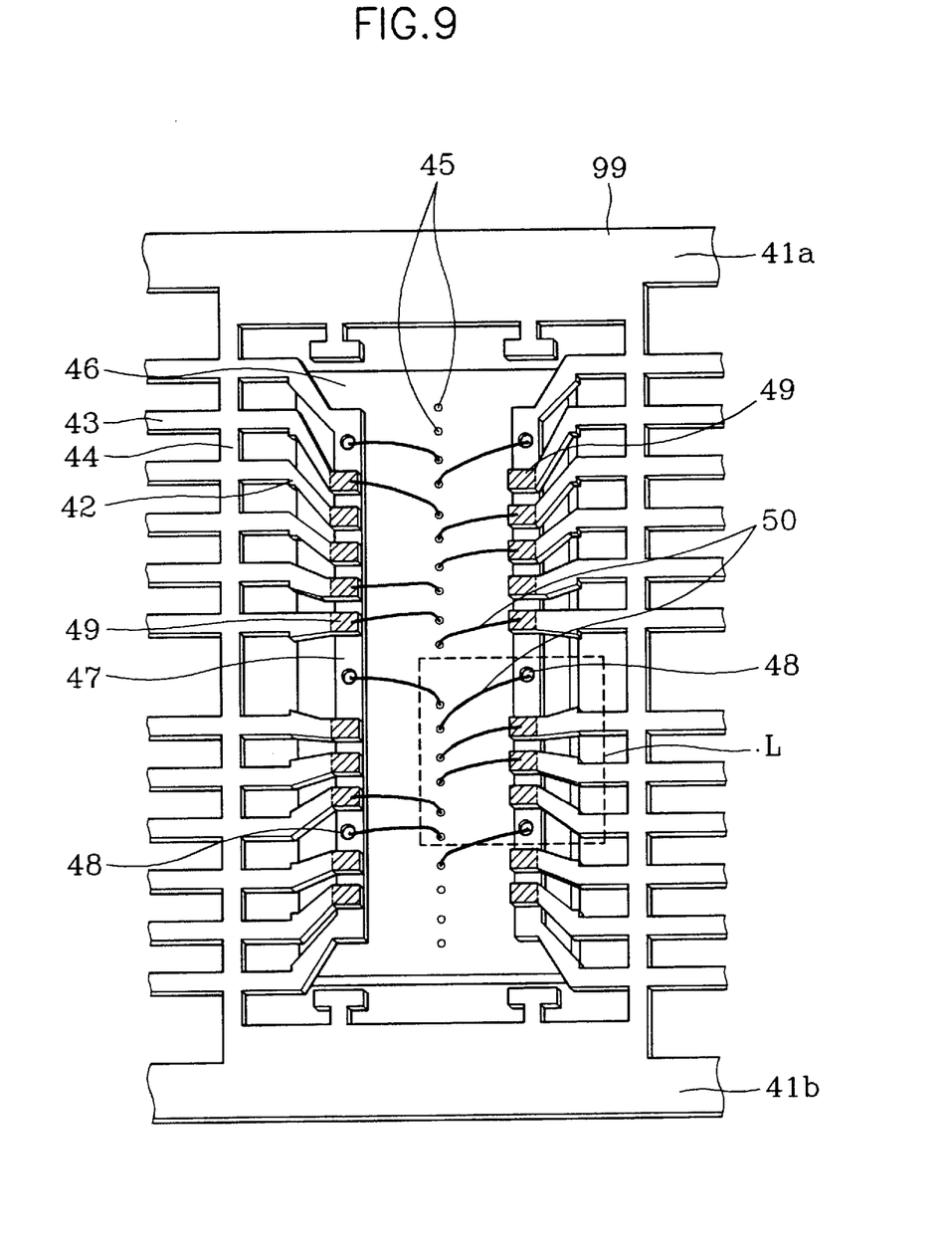
FIG. 9 is a configuration diagram of a second embodiment of an LOC lead frame on which a semiconductor chip is attached.

Referring to FIG. 9, the second embodiment of the lead frame 99 of the present invention comprises upper and lower side rails 41a and 41b formed above and under the lead frame 99, inner and outer leads 42 and 43 formed between upper and lower side rails 41a and 41b, a dam bar 44 for maintaining a desired distance between the inner and outer leads 42 and 43 the upper and lower side rails 41a and 41b, a semiconductor chip 46 located under inner leads 42 and having a plurality of bonding pads 45 on its top surface, and bus bars 47 made of a conductor and extending from a portion of the inner leads 42 to under the front end of inner leads 42.

Figure 11:
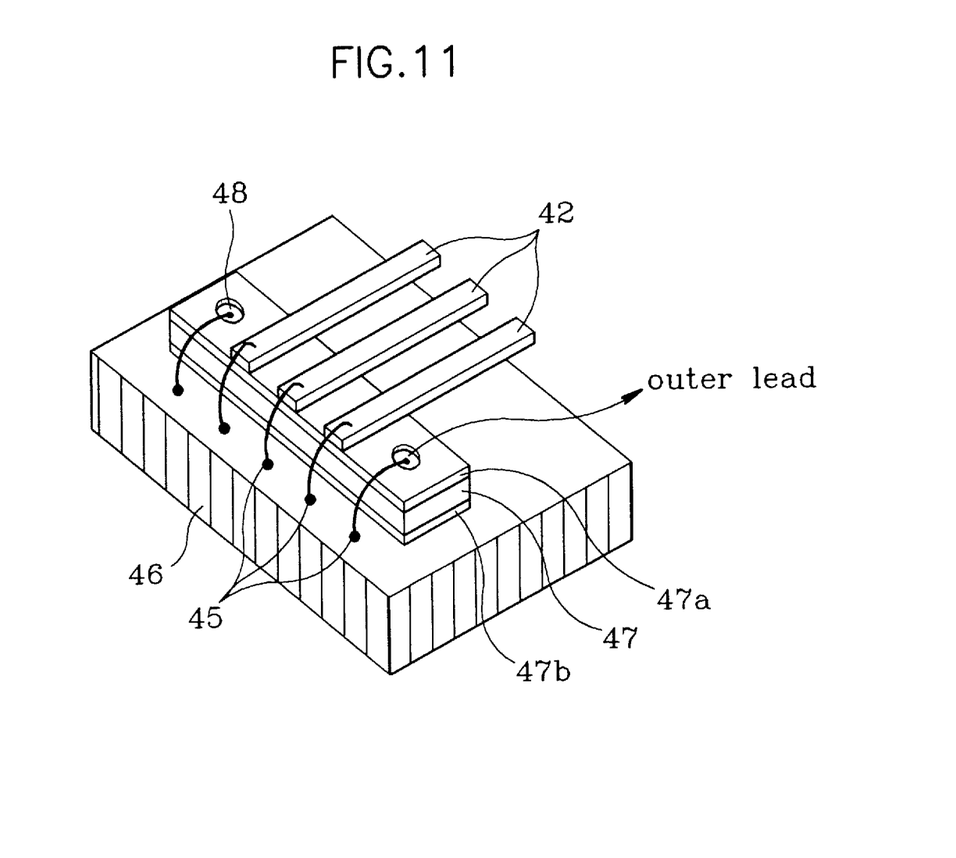
FIG. 11 is an enlarged view of area L of FIG. 9.

Open areas 48 are provided on the top surface of bus bars 47. As illustrated in FIG. 11, a first insulation double-sided adhesive tape 47a for attaching the bottom surface of the front end of inner leads 42 to the top surface of bus bars 47 is formed thereon. A second double-sided insulation tape 47b for attaching the bottom surface of bus bars 47 to the top surface of semiconductor chip 46 is formed on the bottom surface of bus bars 47.

Here, open areas 48 formed on first insulation adhesive tape 47a are used for wire bonding between bus bars 47 exposed therethrough and the bonding pads 45 of semiconductor chip 46. Bus bars 47 are used as a common power supply bar for supplying power to outer leads 43 or semiconductor chip 46. Reference numeral 49 is a conductor such as silver coated for wire bonding between inner leads 42 and bonding pad 45. Reference numeral 50 is a wire.

The second embodiment of the present invention does not use a separate double-sided adhesive insulation tape for attaching the inner leads 42 and semiconductor chip 46. Instead, bus bars 47 are placed under the front end of inner leads 42, and the first insulation adhesive tape 47a having open areas 48 is formed on the top surface of bus bars 47. By doing so, the bottom surface of the front end of inner leads 42 is attached to the top surface of bus bars 47. Second insulation adhesive tape 47b for attaching the bottom surface of bus bars 47 to the top surface of semiconductor chip 46 is formed on the bottom surface of bus bars 47. In FIG. 9, one, two, or more bus bars 47 may be provided.

Figure 10:
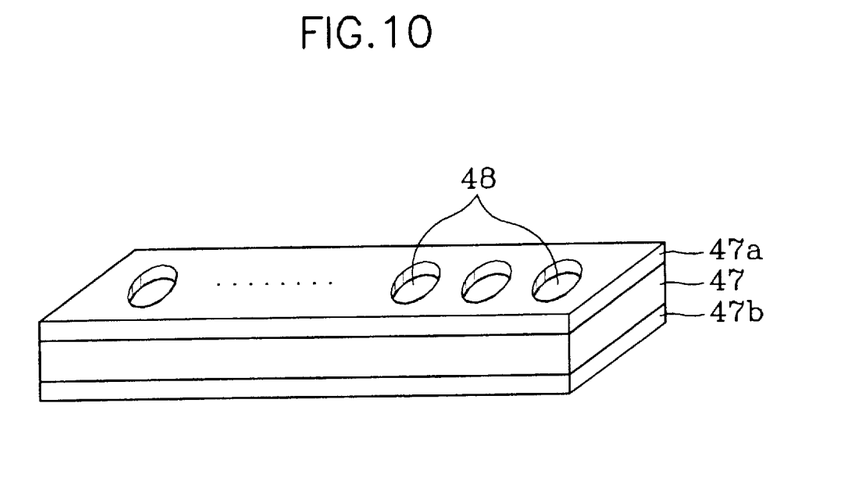
FIG. 10 is a perspective view of the bus bars of FIG. 9.

Referring to FIG. 10, second insulation double-sided adhesive tape 47b, bus bar 47 and first insulation double-sided adhesive tape 47a having open areas 48a are stacked sequentially.

FIG. 11 shows bus bars 47 connected to bonding pads 45 of semiconductor chip 46 (or outer leads 43) via open areas 48 in the first insulation double-sided adhesive tape 47a. Inner leads 42 are attached to bus bars 47 via first insulation double-sided adhesive tape 47a. Semiconductor chip 46 is attached to bus bars 47 via second insulation double-sided adhesive tape 47b.

In the second embodiment, bus bars 47 may be made of a conventional iron-nickel alloy, copper or aluminum. The thickness of bus bars 47 is about 50 $\mu$m which is suitable in the current size of the LOC semiconductor package. However, the size of the bus bars 47 can be varied, if necessary.

Bus bars 47 may be made by two different methods. First, the bus bars 47 can be made during manufacture of the lead frame 99. Alternatively, the bus bars 77, can be separately made from the lead frame 99 and later attached in advance on the top surface of semiconductor chip 46 as the lead frame is arranged on semiconductor chip 46.

For the final steps of the process, other package elements (excluding the outer leads 43) are encapsulated during molding and the outer leads 33 are formed in a desired shape.

Third Embodiment

Figure 12:
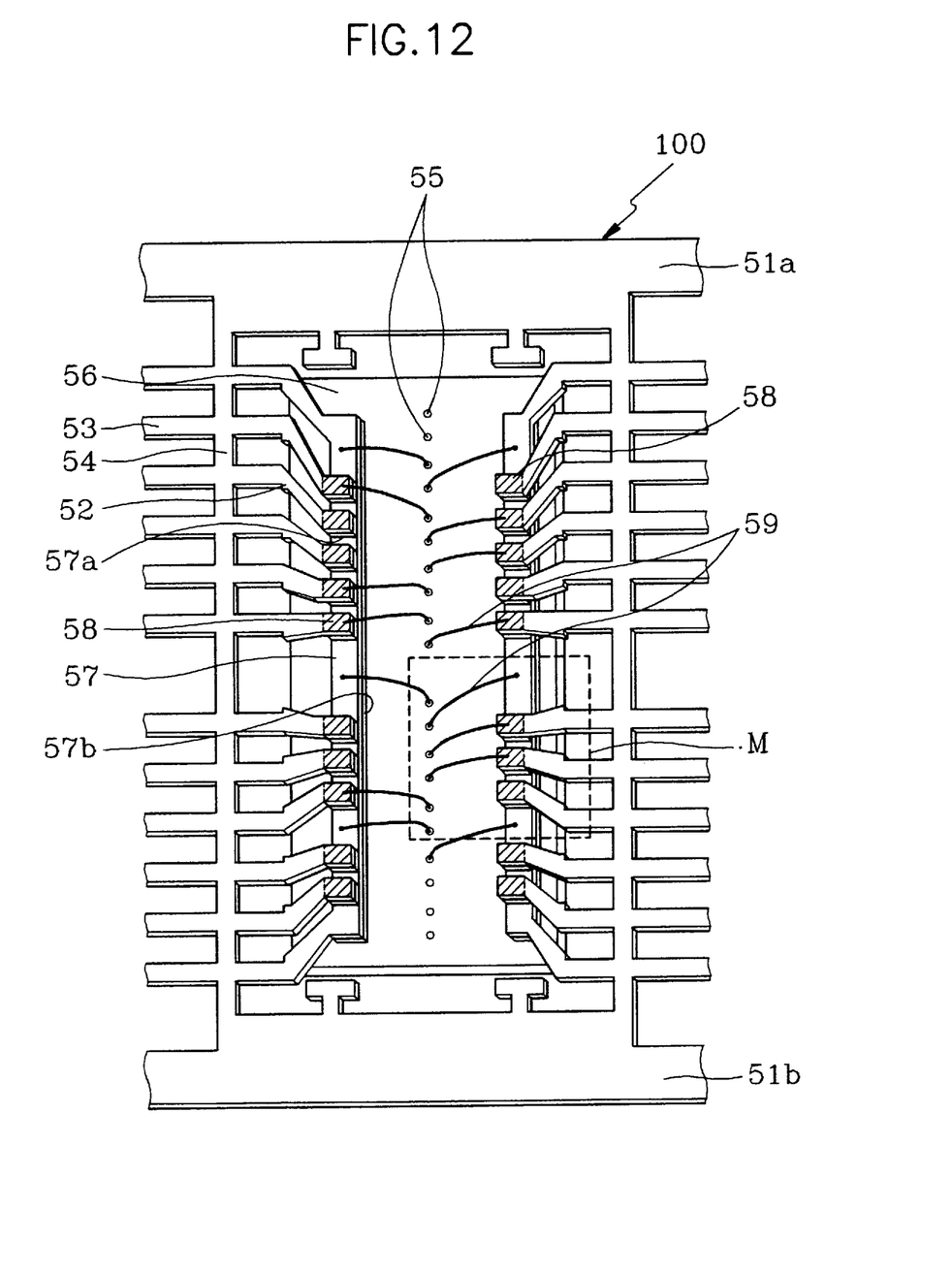
FIG. 12 is a configuration diagram of a third embodiment of an LOC lead frame on which a semiconductor chip is attached.

Hereinafter, the third embodiment of the present invention of the LOC lead frame 100 on which a semiconductor chip is attached will be described with reference to the attached drawings. Referring to FIG. 12, the LOC lead frame 100 is substantially the same as that of the second embodiment shown in FIGS. 9–11, except for the structure of the bus bars.

The third embodiment of the lead frame 100 of the present invention comprises upper and lower side rails 51a and 51b formed above and under the lead frame 100, inner and outer leads 52, 53 formed between upper and lower side rails 51a, 51b, a dam bar 54 for maintaining the distance between inner and outer leads 52, 53 between upper and lower side rails 51a, 51b, a semiconductor chip 56 located under inner leads 52 and having a plurality of bonding pads 55 on its top surface, and bus bars 57 made of a conductor and extending from part of inner leads 52 to under the front end of inner leads 52.

Though not fully shown in FIG. 12, insulation adhesive islands 57a for attaching the bottom surface of the front end of inner leads 52 to the top surface of bus bars 57 are formed on the top surface of bus bars 57. An insulation double-sided adhesive tape 57b for attaching the bottom surface of bus bars 57 to the top surface of semiconductor chip 56 is formed on the bottom surface of bus bars 57.

Here, the exposed surfaces of bus bars 57 not covered by insulation adhesive islands 57a are used for wire bonding to bonding pad 55 of semiconductor chip 56 or outer leads 53. In FIG. 12, one, two or more bus bars 57 may be provided.

Figure 13:
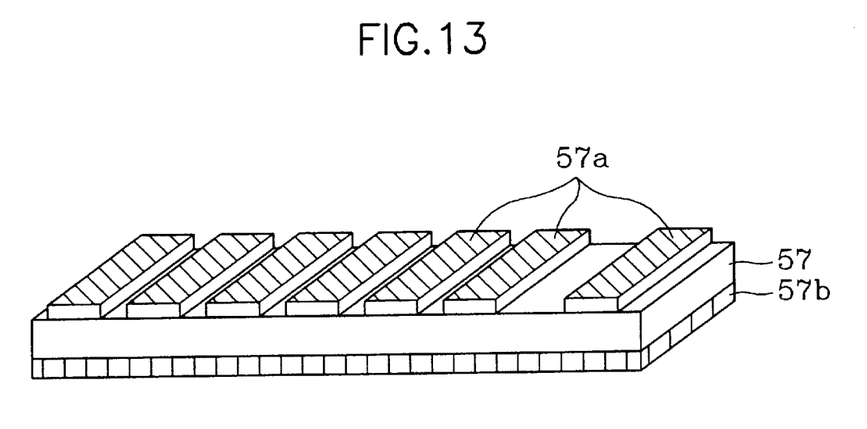
FIG. 13 is a perspective view of the bus bars of FIG. 12.

In FIG. 13, insulation adhesive island 57a for attaching the bottom surface of the front end of inner leads 52 to the top surface of bus bars 57 are formed on the top surface of bus bars 57. A double-sided insulation adhesive tape 57b for attaching the bottom surface of bus bars 57 to the top surface of semiconductor chip 56 is formed on the bottom surface of bus bars 57.

Figure 14:
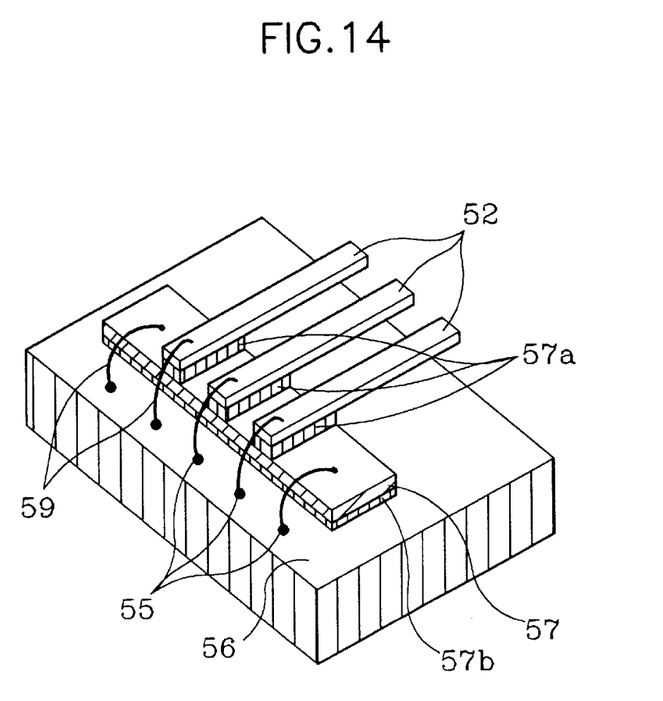
FIG. 14 is a partially enlarged view of area M of FIG. 12.

In FIG. 14, the portion of bus bars 57 not covered by insulation adhesive islands 57a is wire-bonded to bonding pads 55 of semiconductor chip 56 or outer leads 52. Each of the inner leads 52 is attached to the top surface of bus bars 57 by one of the insulation adhesive islands 57a. The bottom surface of bus bars 57 is attached to the top surface of semiconductor chip 56 by double-sided insulation adhesive tape 57b.

In FIG. 12, reference numeral 58 indicates a conductive material coated on the top surface of the front end of inner leads 52 in order to facilitate wire-bonding of inner leads 52 to bonding pads 55 of semiconductor chip 56. Reference numeral 59 identifies wires used in the wire bonding. The detailed description of the remainder of the third embodiment is similar to the second embodiment and, as such, is omitted.

The second and third embodiments have the following advantages.

Firstly, unlike the conventional art in which the bus bars and inner leads are formed at the same height on the semiconductor chip, the bus bars are lower than the inner leads, thereby preventing an electrical short between the bus bars and inner leads regardless of the height of the wire loop in wire bonding.

Secondly, an insulation wall is not formed nor an insulator coated on the bus bars in order to prevent an electrical short between the bus bars and inner leads. Elimination of this step reduces the production cost and simplifies the overall process.

Thirdly, the height of wire loop is lowered in wire bonding, making compact semiconductor package easier to manufacture.

Fourthly, the front end of the inner leads is placed on the top surface of the bus bars, not on the same plane. Shortening the length of wire for connecting the inner leads and bonding pads in wire bonding prevents the wire from sagging.

Fifthly, the shortening of the wires between the inner leads and bonding pads reduces the transmission length of signals.

The invention being thus described, it will be obvious that the same may be varied in many ways. Such variations are not to be regarded as a departure from the spirit and scope of the invention and all such modifications as would be obvious to one skilled in the art are intended to be included within the scope of the following claims.

What is claimed is:

1. A semiconductor package comprising:
    a semiconductor chip having a plurality of bonding pads on its top surface;
    a plurality of inner leads located above said semiconductor chip;
    a plurality of outer leads extending from said respective inner leads;
    at least one bus bar for power supply and ground and extending continuously from part of said plurality of inner leads to under front ends of the plurality of inner leads of said semiconductor chip;
    a first insulation adhesive tape having a plurality of open areas attaching a top surface of said bus bar to a plurality of bottom surfaces of said front ends of said inner leads;
    a second insulation adhesive tape attaching a bottom surface of said bus bar to the top surface of said semiconductor chip;
    a plurality of wires for electrical connection between said inner leads and said bonding pads and between said bus bar and said bonding pads through said open areas; and
    a compound body molded with all the other package elements excluding said outer leads.

2. A semiconductor package as claimed in claim 1, further comprising: a plurality of conductors coated on the top surface of the front end of said inner leads so as to facilitate wire bonding between said inner leads and bonding pads.

3. A semiconductor package as claimed in claim 1, wherein said first insulation adhesive tape, second insulation adhesive tape and bus bar are integrally formed.

4. A semiconductor package as claimed in claim 1, wherein an electrical connection between said bonding pads, said bus bar, and said inner leads forms a power supply and ground electrical path.

5. A semiconductor package as claimed in claim 1, wherein said bus bar does not extend beyond said front end of said inner leads.

6. A semiconductor package as claimed in claim 1, wherein said open areas are located adjacent to a group of inner leads, said group of inner leads comprising of at least two inner leads without an open area therebetween.

7. A semiconductor package comprising:
    a semiconductor chip having a plurality of bonding pads on its top surface;
    a plurality of inner leads located above said semiconductor chip;
    a plurality of outer leads extending from said respective inner leads;
    at least one bus bar for power supply and ground and extending continuously from part of said plurality of inner leads to under front ends of the plurality of inner leads of said semiconductor chip;

a plurality of insulation adhesive islands formed on a top surface of said bus bar and attaching a plurality of bottom surfaces of said front ends of said inner leads to said bus bar;

an insulation adhesive tape attaching a bottom surface of said bus bar to the top surface of said semiconductor chip;

a plurality of wires for electrical connection between said inner leads and bonding pads and between said bus bar and said bonding pads; and a compound body molded with all the other package elements excluding said outer leads.

8. A semiconductor package as claimed in claim 7, further comprising: a plurality of conductors coated on the top surface of the front end of said inner leads so as to facilitate wire bonding between said inner leads and bonding pads.

9. A semiconductor package as claimed in claim 7, wherein said insulation adhesive islands, bus bar and insulation adhesive tape are integrally formed.

10. A semiconductor package as claimed in claim 7, wherein an electrical connection between said bonding pads, said bus bar, and said inner leads forms a power supply and ground electrical path.

11. A semiconductor package as claimed in claim 7, wherein said bus bar does not extend beyond said front end of said inner leads.

12. A semiconductor package as claimed in claim 7, wherein said electrical connections between said bus bar and said bonding pads are located adjacent to a group of inner leads, the group of inner leads comprising of at least two inner leads without an electrical connection therebetween.

* * * * *